(12) United States Patent
Matusch (10) Patent No.: US 8,708,951 B2
(45) Date of Patent: Apr. 29, 2014

(54) INJECTOR AND DUAL-CHAMBER SYSTEM HAVING STERILE COMPONENTS

(75) Inventor: Rudolf Matusch, Marburg (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 110 days.

(21) Appl. No.: 12/932,268

(22) Filed: Feb. 22, 2011

(65) Prior Publication Data

US 2011/0152758 A1 Jun. 23, 2011

Related U.S. Application Data

(63) Continuation-in-part of application No. PCT/EP2009/006066, filed on Aug. 21, 2009.

(30) Foreign Application Priority Data

Sep. 25, 2008 (DE) .......................... 10 2008 048 981

(51) Int. Cl.
    *A61M 37/00* (2006.01)
(52) U.S. Cl.
     USPC .............................................. 604/88; 604/68
(58) Field of Classification Search
     USPC ......... 604/83, 87, 89, 68, 69, 70, 71, 237, 90, 604/91, 92, 82, 88
     See application file for complete search history.

(56) References Cited

U.S. PATENT DOCUMENTS

| | | | |
|---|---|---|---|
| 3,610,297 A | 10/1971 | Raaf | |
| 3,946,732 A | 3/1976 | Huscham | |
| 5,649,912 A | 7/1997 | Peterson | |
| 5,993,412 A * | 11/1999 | Deily et al. | 604/68 |
| 6,174,304 B1 | 1/2001 | Weston | |
| 6,223,786 B1 | 5/2001 | Castellano | |
| 6,881,200 B2 * | 4/2005 | Bellhouse et al. | 604/68 |
| 2001/0027290 A1 * | 10/2001 | Weston | 604/72 |
| 2001/0051789 A1 | 12/2001 | Parsons | |
| 2005/0113747 A1 | 5/2005 | Moir | |
| 2008/0172001 A1 * | 7/2008 | Reynolds et al. | 604/232 |
| 2010/0024967 A1 | 2/2010 | Gritti et al. | |

FOREIGN PATENT DOCUMENTS

| | | |
|---|---|---|
| CA | 2 356 614 A1 | 4/2000 |
| EP | 1 336 419 A1 | 8/2003 |
| WO | WO 01/87385 A1 | 11/2001 |
| WO | WO 2004/032997 A2 | 4/2004 |

* cited by examiner

*Primary Examiner* — Jason Flick
*Assistant Examiner* — Brooke Matney
(74) *Attorney, Agent, or Firm* — R. S. Lombard; K. Bach (57) ABSTRACT

The invention relates to a single-use injector (4) and a dual-chamber system (99), wherein at least one first chamber (105) is part of a cylinder-piston unit (100) that can be received in the single-use injector, and wherein the second chamber (255) is part of a container (250) that can be at least temporarily closed by means of a stopper (257) and that is inserted in a container adapter (200) releaseably supported on the single-use injector. To this end, the plug comprises a plug hole. The container adapter comprises a transfer tube that is closed at first. When the container is inserted in the container adapter, the transfer tube (242) connects the interior of the cylinder-piston unit to the interior of the container.

5 Claims, 5 Drawing Sheets

INJECTOR AND DUAL-CHAMBER SYSTEM HAVING STERILE COMPONENTS

CROSS-REFERENCE TO RELATED APPLICATION

This is a continuation-in-part application of pending international application PCT/EP 2009/006066 filed Aug. 21, 2009 and claiming priority of German Application No. 10 2008 048 981.6 filed Sep. 25, 2008.

BACKGROUND OF THE INVENTION

The invention relates to a single-use injector and a two-chamber system, at least a first chamber being part of a cylinder/piston unit which can be received in the single-use injector and the second chamber being part of a container which is closed at least temporarily by means of a stopper and inserted in a container adapter which is detachably mounted on the single-use injector.

A single-use injector of this type and a two-chamber system are known, for example, from the subsequently published DE 10 2008 003 103 A1. If the individual components are manufactured on different production lines and/or staggered over time, there is the risk of contaminations.

It is an object of the present invention of developing a single-use injector and a two-chamber system in which the solvent, for example water, and the pharmaceutical composition, for example lyophilisate, are sterile, can be combined in a sterile manner, dissolved in a sterile manner and applied in a sterile manner.

SUMMARY OF THE INVENTION

The invention relates to a single-use injector (4) and a dual-chamber system (99), wherein at least one first chamber (105) is part of a cylinder-piston unit (100) that can be received in the single-use injector, and wherein the second chamber (255) is part of a container (250) that can be at least temporarily closed by means of a stopper (257) and that is inserted in a container adapter (200) releaseably supported on the single-use injector. To this end, the plug comprises a plug hole. The container adapter comprises a transfer tube that is closed at first. When the container is inserted in the container adapter, the transfer tube (242) connects the interior of the cylinder-piston unit to the interior of the container.

The present invention provides that the stopper (257) comprises a stopper hole (254). The container adapter has an initially closed transfer tube. When the container is inserted into the container adapter, the transfer tube connects the interior of the cylinder/piston unit to the interior of the container.

Preferably, the transfer tube (242) is initially closed by means of a membrane cap (290). The stopper hole (254) is preferably initially closed by means of a membrane (256). Preferably, when the container (250) is inserted into the container adapter (200), the transfer tube (242) pierces both membranes (256, 292). The container adapter (200) desirably has at least two locking elements (223, 224) which are offset from one another in the container insertion direction (7). Preferably, the container adapter (200) comprises a container receptacle (221) with at least one at least approximately radially oriented slide recess (228). The slide recess (228) is desirably covered by means of a valve hose (229). Preferably, the joint between the container (250) and the inner wall of the container receptacle (221) is closed in a sterile manner by means of a ring seal (217). The transfer tube hole (244) preferably opens into a transverse hole (245) penetrating the transfer tube (242). The transverse hole (245) may be aligned with two slide recesses (228). Preferably, the membrane cap (290) has an elastically deformable wall region (291). The container (250) is desirably a second cylinder/piston unit (250).

BRIEF DESCRIPTION OF THE DRAWINGS

Further details of the invention emerge from the schematically illustrated embodiments as shown in the following drawings, in which.

DETAILED DESCRIPTION OF PARTICULAR EMBODIMENTS

Figure 1:
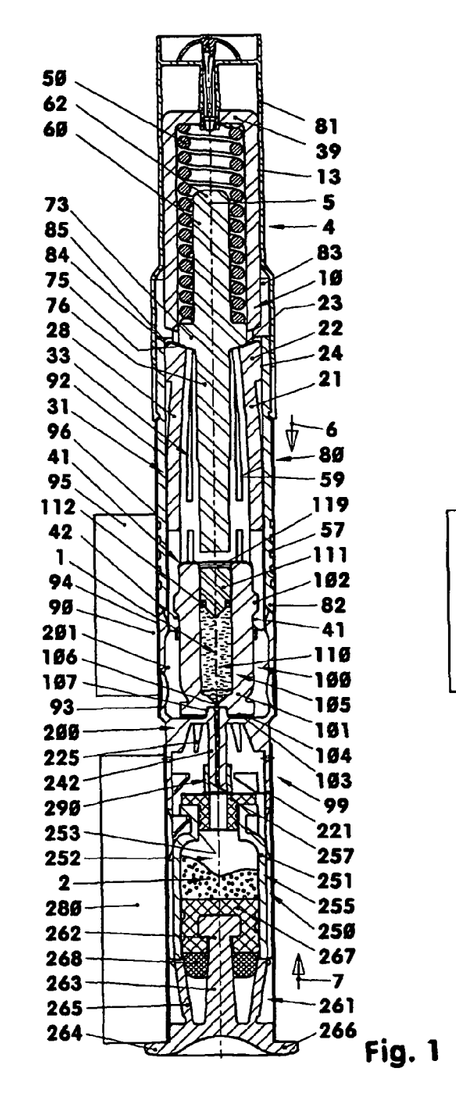
FIG. 1 shows a single-use injector and two-chamber system.
Figure 2:
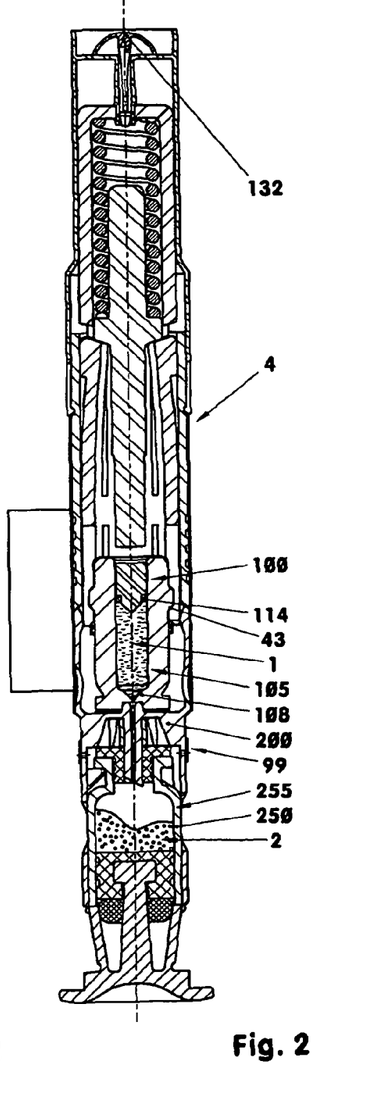
FIG. 2 shows the single-use injector after the container has been inserted.
Figure 3:
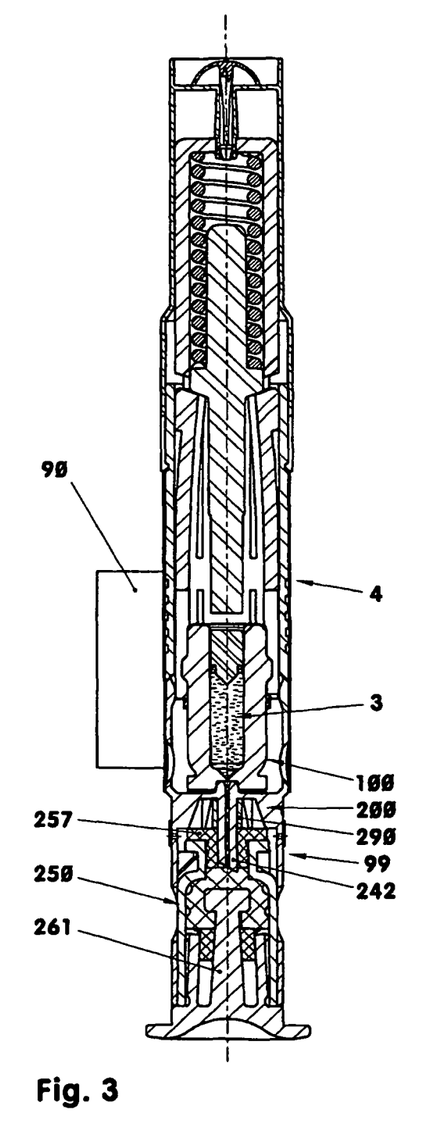
FIG. 3 shows the single-use injector after the transfer by pumping.
Figure 4:
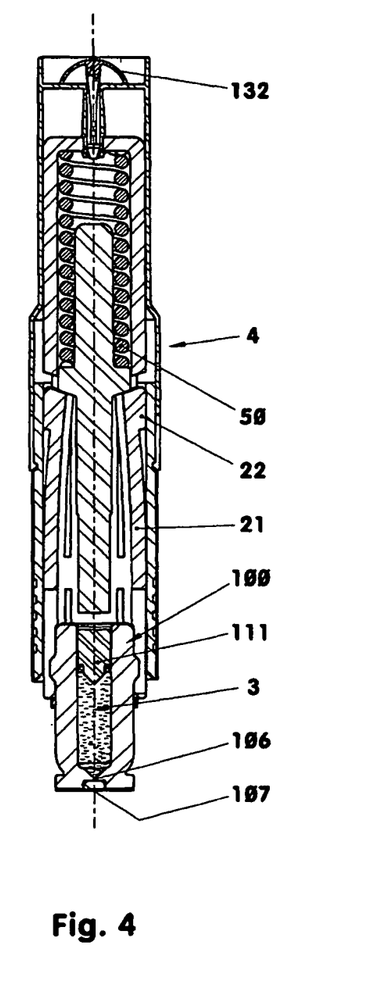
FIG. 4 shows the single-use injector with the cylinder/piston unit prior to triggering.
Figure 5:
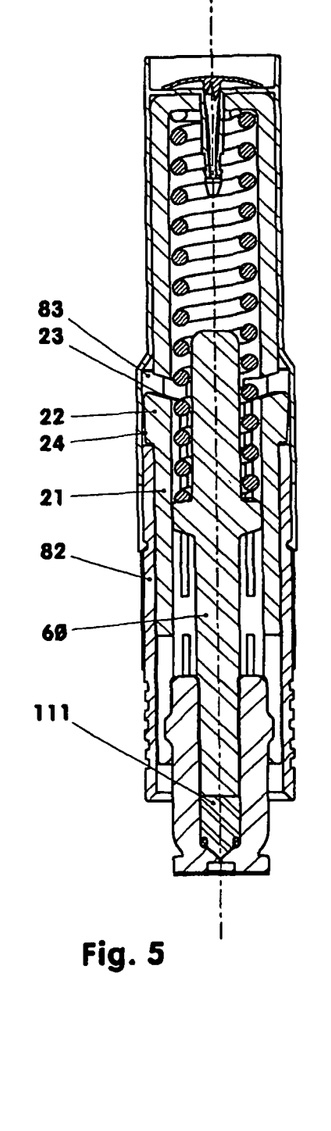
FIG. 5 shows FIG. 4 after triggering.

FIGS. 1-5 show a single-use injector (4) and a two-chamber system (99) adapted thereto. FIG. 1 shows, for example, the state of delivery to the user, in which the single-use injector (4) is pre-tensioned, the first chamber (105) is, for example, partially filled with solvent and the second chamber (255) is, for example, partially filled with lyophilisate and both chambers (105, 255) are separated from each other. In the illustration of FIG. 2, the two chambers (105, 255) are joined together to produce an injection solution. FIG. 3 shows the single-use injector (4) and the two-chamber system (99) after the production of the injection solution and FIG. 4 shows this injector (4) with the injector-side chamber (105) prior to triggering. In the illustration of FIG. 5, the needleless single-use injector (4) is triggered and the injection solution (3) has been sprayed out.

The single-use injector (4) illustrated in FIGS. 1-5 comprises a housing (10), a piston actuating plunger (60) and a helical compression spring (50) as the spring energy store. In addition, a triggering unit (80) with a triggering element (82) and a securing element (90) are arranged on the housing (10).

The housing (10) is a one-piece, pot-shaped, downwardly open hollow body with an elevated floor (39). The housing is made, for example, from a glass fibre-reinforced polyamide by injection-moulding. The housing (10) has a substantially tubular form and is divided into two functional regions: on the one hand, the upper envelope region (31) and, on the other hand, the lower fixing region (41).

In the envelope region (31), the housing (10) has, for example, two mutually opposing, window-like apertures (33). A respective press rod (21), as a resilient bending bar, is moulded onto the lower edge of the individual aperture (33). The moulding-on site for the press rods (21) is positioned just above the fixing region (41). For forming each press rod (21), a narrow, at least roughly U-shaped gap, which surrounds the individual press rod (21) to the side and top, is located in the lower region of the envelope portion (31).

The press rod (21) has, for example over 80% of its length, the wall thickness and the curvature of the wall of the housing (10). This region has inter alia also the function of a resilient bending bar (28). It has a crescent-shaped cross section.

If appropriate, a portion of this bending bar (28) can also be equipped with a rectangular cross section in order to reduce bending stresses which occur during use in the edge region of the bending bar.

In the case of injectors in which the piston actuating plunger (60) is—at least in certain portions—guided straight with a low degree of play in the housing (10) and the piston actuating plunger (60) has sufficient bending strength, use may also be made of just a single press rod (21) instead of two or more press rods (21).

The—in this case—upper free end of the individual press rod (21) is formed by the radially outwardly protruding cam (22). The cam has at least one support surface (23) oriented in the direction of the centre line (5) and an abutment surface (24) facing away from the centre line (5).

The lower half of the housing (10) is surrounded by the sleeve-like triggering element (82). The triggering element is, for example, embodied in a substantially cylindrical manner and made, for example, of acrylonitrile butadiene styrene (ABS) copolymer. The triggering element (82) is longitudinally displaceably mounted on the radial outer surface (13) of the housing (10). It ends rearwardly with a sharp edge (85) which is part of an end-side, set-back flank (84) of the triggering element (82). According to FIG. 1, below the edge (85), the outward abutment surfaces (24) of the cams (22), which are moulded onto the press rods (21), touch the inner wall (59) of the triggering element (82) in a securing manner.

For example, close to the edge (85), a triggering cap (81), which completely surrounds the trailing end of the housing (10), is fastened to the triggering element (82). The triggering cap (81) comprises a peripheral widening (83) in which the cams (22) are received on triggering of the injector, cf. FIG. 5. In the case of a non-rotationally symmetrical triggering element (82), partial widenings or non-covered openings may also be present for each press rod (21), instead of this widening (83). Above the widening (83), the triggering cap (81) rests against the outer wall (13) of the housing (10) in a slidable manner.

The piston actuating plunger (60), which is arranged in the housing (10), is divided into two regions. The lower region is the piston slide (76). Its diameter is somewhat smaller than the internal diameter of the rear region of the cylinder (101) of a cylinder/piston unit (100). The lower end face of the piston slide (76) acts directly on the piston (111) of this cylinder/piston unit (100).

The upper region of the piston actuating plunger (60), the plunger plate (73), is a flat disc which is cylindrical at least in certain regions and the external diameter of which is smaller by a few tenths of a millimeter than the internal diameter of the housing (10) in the envelope region (31). The lower end side has a collar surface (75) which is arranged around the piston slide (76). The collar surface has the shape of a frustoconical envelope, the apex angle of which is approx. 100 to 140 degrees. In the illustrated exemplary embodiment, the collar surface (75) has an apex angle of 140 degrees. The notional apex of the frustoconical envelope rests on the centre line (5) in the region of the piston slide (76). The collar surface (75) can also be spherically curved.

Obviously, the piston slide (76) may also be embodied as a separate component in isolation from the plunger plate (73). For this purpose, the piston slide is then guided on the inner wall of the housing (10).

The helical compression spring (50) sits pre-tensioned between the plunger plate (73) and the elevated floor (39) of the housing (10). The helical compression spring (50) is supported on the floor (39) of the housing (10). The spring force of the helical compression spring (50) is transmitted to the press rods (21) via the plunger plate (73). Owing to the inclination of the collar surface (75), the press rods (21) are urged radially outward in the manner of a wedge gear. The triggering sleeve (82) permanently supports this radial force.

The piston actuating plunger (60) has a guide pin (62) above the plunger plate (73). The guide pin guides the helical compression spring (50) or is guided thereby. The piston slide (76) is located below the plunger plate (73), centrally in the extension of the guide pin (62).

The fixing region (41) for receiving the installable cylinder/piston unit (100), which comprises the first chamber (105), is located below the envelope portion (31). The fixing region (41) comprises, for example, eight spring hooks (42) oriented parallel to the centre line (5). The spring hooks (42) each have an at least two-flanked rear grip (43) for receiving the cylinder/piston unit (100) without play. The mutually opposing flanks of the rear grip (43) enclose an angle of, for example, 90 angular degrees. The length and the spring rate of the spring hooks (42) are designed in such a way that the cylinder/piston unit (100) can be installed without plastic deformation of the spring hooks (42).

In the exemplary embodiment, the cylinder/piston unit (100) consists of a transparent cylinder (101) which can be filled with water for injection purposes (1) or an injection solution (3). The water for injection purposes (1) can already contain active substances. In the illustration of FIG. 1, the piston (111) is in the rear position. Above the piston (111), the piston actuating plunger (60) is, for example, arranged in the housing (10) in such a way that, although it does not touch the piston (111), it is laterally guided by its lower end, for example in the upper region of the cylinder (101).

The cylinder (101) is, for example, a clearly visible, thick-walled pot, the optionally cylindrical outer wall of which carries a, for example peripheral, locking ring (102) which rests in a dimensionally stable manner against the flanks of the rear grip (43) of the spring hooks (42). The rodless piston (111) sits in the, for example cylindrical, hole of the cylinder (101). At its front, at least roughly conically configured end face, the piston (111) has an axial annular groove (112) for receiving a ring seal (114) or a permanently resilient sealing compound. A, for example cylindrical, metal plate is, if appropriate, embedded in the trailing end face of the piston (111).

A short, cylindrical, nozzle-like hole (106) is located at the centre of the hole of the cylinder (101), the cylinder floor of which is at least roughly adapted to the contour of the front piston end side. The diameter of the nozzle-like hole is approx. 0.1 to 0.5 millimeters. This hole (106) is one to five times as long as its diameter. It ends in a cylindrical recess (107) of the floor-side, outer end face (103) of the cylinder (101). In order to increase application safety, this end face (103) can additionally be provided with an adhesive ring (104).

The back of the cylinder (101) is closed in a sterile manner by a sterile filter membrane (119).

Figure 6:
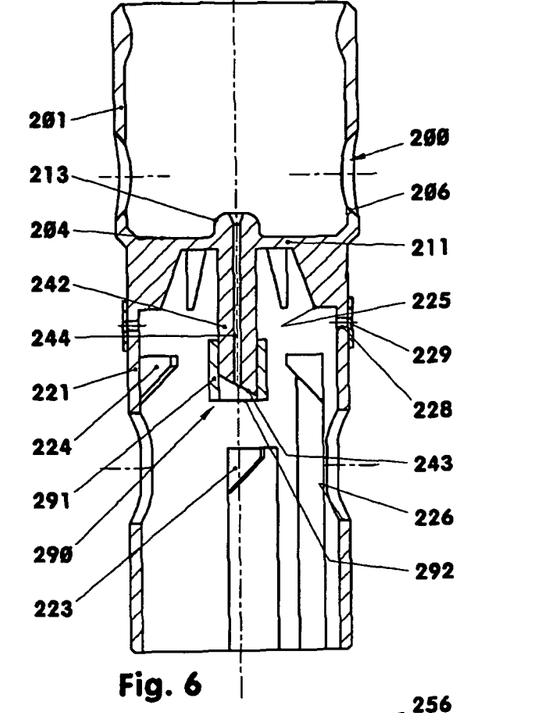
FIG. 6 shows the container adapter with the cap.

Furthermore, a container adapter (200) is inserted into the single-use injector (4). The container adapter is a bushing-like component which receives, for example, the second chamber (255)—the second chamber comprises in this case a container (250) embodied as a cylinder/piston unit (250)—in a container region (221). At the same time, the container adapter has a sleeve-like adapter region (201) with which it sits longitudinally displaceably in the housing (10). FIG. 6 shows the container adapter (200) with a membrane cap (290) as an individual part.

The adapter region (201) is a cylindrical cup which surrounds at least the lower fifth of the cylinder (101) with a spacing. The adapter region has two mutually opposing, for example circular, windows (206) and an annular shoulder (204) on the intermediate floor (211). The windows (206) may be dispensed with if the container adapter material is transparent.

A transfer tube (242), which joins the adapter region (201) and the container region (221) together, is arranged centrally in the intermediate floor (211). For centring at the recess (107), the surface facing the adapter region (201) has a central elevation (213). The transfer tube (242) has, for example, an external diameter of four millimeters. In the exemplary embodiment, its length is five times the external diameter and its minimum internal diameter, the diameter of the hole (244), corresponds to at least the diameter of the nozzle-like hole (106). The minimum diameter of the hole (244) may be, for example, one millimeter. For example, the diameter of the hole (244) can taper, for example conically, from both end sides toward the centre or from one end side toward the other. The dimensions of the external diameter of the transfer tube (242) are such that the transfer tube (242) sits tight in the hole (254) of a stopper (257).

A pot-shaped membrane cap (290) is firmly adhered to the bevelled end side, facing the container region (221), of the transfer tube (242). The membrane cap comprises a, for example cylindrical, elastically deformable wall region (291) and an end side embodied as a membrane (292). The membrane (292) can also be moulded onto the wall region (291). The wall thickness of the wall region (291) is, for example, one millimeter.

The container region (221) has, for example, two groups of locking elements (223, 224) which are set apart from the intermediate floor (211) by different distances. The individual locking element (223, 224) is, for example, a triangular element protruding non-radially from the inner wall of the container region (221), cf. FIGS. 6 and 12.

Furthermore, at least two roughly radially arranged slide recesses (228) are arranged in this region (221). The term "at least roughly" means in this case that the centre line of the hole can enclose with a radial line an angle of up to 45 degrees. During the manufacture of the container adapter (200), the transfer tube (242) is supported, for example, by means of slides which are guided through these slide recesses (228). If appropriate, a slide recess (228) may be dispensed with. In the illustration of FIGS. 1 and 2, the slide recesses (228) are covered by a valve hose (229).

The cylinder/piston unit (250) is arranged in the container region (221). The external diameter of the cylinder/piston unit is just slightly smaller than the internal diameter of the container region (221).

Figure 7:
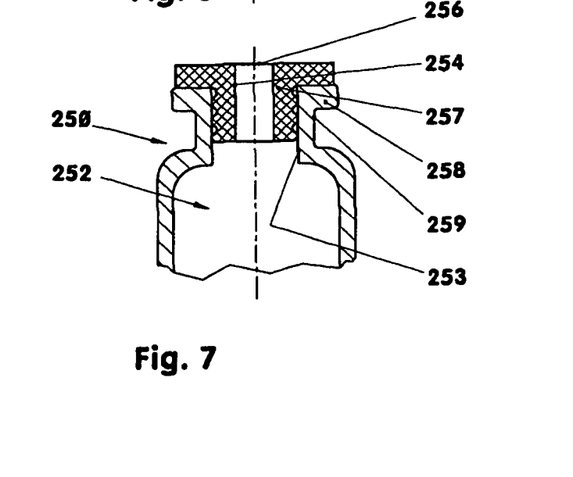
FIG. 7 shows the detail of the container with the stopper.

The cylinder/piston unit (250) has a cylinder which is formed from a transparent tube (251), for example a glass or plastic material tube, such as, cyclic olefin copolymer (COC), and a resilient stopper (257). The stopper (257), cf. FIG. 7, rests on the flange edge (258) of the glass tube (251). The stopper also has a, for example central, pot-like, stopper hole (254), of which the end side, which in FIG. 7 is directed outward, is embodied as a membrane (256). The stopper bore (254) may also be embodied as an aperture which is closed by means of a membrane (256).

The back of the glass tube (251) is closed by a movable piston (261). The piston (261) consists of a piston rod (262), a rear piston pressure plate (264), a front stopper carrier (263) and a resilient piston stopper (267) placed thereover. In order to hold the piston (261) in its rear position when a vacuum has been created in the cylinder interior (252), the piston (261) additionally has two or more locking elements (265) which are, for example, moulded onto the piston pressure plate (264) and are—resiliently outwardly—supported on the rear edge of the glass tube (251). A resilient rubber ring (268), which presses the locking elements (265) outward, sits on the back of the piston stopper (267).

The piston pressure plate (264) has, toward the glass tube (251), a cylindrical collar (266) which has the same external diameter as the container region (221).

In order to prevent triggering, the container adapter (200) is connected to the triggering element (82) of the injector via the banderole (90). The banderole (90) is a tamper-proof closure embodied as an adhesive label.

The banderole (90) itself is, for example, a strip of paper and/or film which is coated on one side with an adhesive in certain regions. The banderole consists of three separate strips which can each be separated from one another via a perforation (96) or via a different predetermined breaking point. The, in each case peripheral, perforations (96) are positioned above the slots (57) and below the windows (206).

According to FIG. 1, an unwinding banderole (280) is pasted over the container region (221) and the piston (261). The unwinding banderole (280) covers in this case the windows (226) and the locking elements (265) of the piston (261) in a protective manner. In addition, the unwinding film (280) prevents accidental extracting of the container adapter (200) from the housing (10).

During manufacture, the two cylinder/piston units (100, 250) are manufactured, for example, in separate production processes and filled on different production lines. The container adapter (200) is, for example, manufactured separately. The individual parts can thus be produced to stock and not be joined to the single-use injector until later. The components (1-3) are sterile and can be stored in a sterile manner. All the parts which may enter into contact with active substances and/or solvent are, for example, packaged in a sterile manner.

For packing, the first cylinder/piston unit (100) is, for example, inserted into the single-use injector (4) and interlocked. The container adapter (200) is also inserted into the single-use injector (4). In this case, the cap (290) remains on the transfer tube (242). The second cylinder/piston unit (250) is inserted into the container region (221) and interlocked with the locking hook (223) facing away from the intermediate floor (211). The stopper (257) is closed and does not touch the transfer tube (242).

In order to be able to use the single-use injector, the active substance (2), for example a lyophilisate, stored in the cylinder/piston unit (250) must be dissolved in the liquid (1), for example water for injection purposes or physiological saline solution, present in the cylinder (101) of the cylinder/piston unit (100). For this purpose, the liquid (1) is to be pumped into the container (250).

In a first step, the unwinding banderole (280) is removed from the container region (221) and the container (250) is inserted into the container adapter (200), cf. FIG. 2. The locking elements (223) are outwardly displaced. In this case, the tube (242) pierces the two membranes (292, 256), which rest for example one on the other, and presses itself through the stopper (257), so that the tip (243) of the tube ends in the cylinder interior (252). The pushing movement of the container (250) is ended when the stopper (257) rests against the stops (225). The notches (259) engage with the locking elements (224). The membrane cap (290) is displaced along the transfer tube (242). When the container (250) is inserted, the air which is displaced in the process escapes through the slide recesses (228) of the container region (221).

As a result of the infiltrating of the transfer tube (242) into the cylinder interior (252), the cylinder interior (252) communicates with the cylinder interior (110) of the first cylinder/piston unit (100) via the connecting tube (242). The vacuum of the cylinder interior (252) draws the liquid out of the cylinder (101) of the cylinder/piston unit (100). As the cover covering the back of the cylinder (101) is a sterile filter membrane (119), the drawn-in piston (111) can follow the liquid (1) and enters into abutment with the cylinder floor (108). In the interior (252), the lyophilisate (2) is dissolved in the liquid (1). The dissolving process may be observed via the windows (226).

In a second step, the tear-off banderole (94) is removed as soon as the lyophilisate (2) has dissolved. The slots (57) of the triggering element (82) thus become visible. Now, the injector is positioned in such a way that the cylinder/piston unit (100) lies below the cylinder/piston unit (250). Afterwards, the newly produced solution (3) is to be pumped into the cylinder interior (110) through the transfer tube (242). For this purpose, the piston (261) is first released by radially pressing the locking elements (265) in. Owing to the residual vacuum, the piston stopper (267) is placed onto the surface of the solution (3). The solution (3) is now transferred by pumping to the cylinder interior (110) by applying a slight pressure to the piston (261). The solution (3) pushes the piston (111) ahead of itself. Bubble-free filling of the cylinder interior (110) is checked in transmitted light via the windows (206). Generally, a small portion of the solution (3) is drawn back into the glass tube (251), so that, in addition, the piston (111) does not rest against the sterile filter membrane (119).

In a third step, the container adapter (200) is withdrawn with the cylinder/piston unit (250) from the housing (10). Nevertheless, the injector (4) remains secured.

Once the injector (4) has been placed with the cylinder/piston unit (100) onto the injection site, the block button (132) must be pressed in a last step, for example by the thumb of the hand holding the injector (4), in order to be able to move the triggering element (82) together with the triggering cap (81). The triggering element (82) can now be displaced in the direction of the cylinder/piston unit (100). During this process, the triggering element (82) slides on the outer wall (13) of the housing (10) linearly downward, i.e. in the direction of the injection site. The abutment surfaces (24) of the press rods (21) slip via the edge (85) and jump, under the force of the spring element (50), so as to release radially outward into the widening (83). The press rods (21) have bent resiliently outward and are now in their actual starting position. The press rods (21), which are now no longer deformed, release the piston actuating plunger (60), so that the piston slide (76) moves jerkily toward the sterile filter membrane (119) of the cylinder (101) under the action of the spring element (50). The sterile filter membrane (119) is pierced and the piston (111) is moved downward for draining the cylinder (101), cf. FIG. 5. The cylinder (100) is drained.

FIGS. 8 to 11 show a single-use injector (4) and a two-chamber system (99), the second chamber (255) of which has a container (250) having a constant container volume.

The single-use injector (4) is constructed in a similar manner to the single-use injector (4) illustrated in FIGS. 1-5. However, the piston (111) has on its back a, for example central, frustoconical envelope-shaped recess (115) into which a pump rod (140) is screwed by means of a conical thread (141), cf. FIG. 11. The piston actuating plunger (60) has a, for example central, hole (63) through which the pump rod (140) passes with a high degree of play. The pump rod (140), which protrudes from the single-use injector (4), can be released from the piston (111) with the expenditure of little force.

A transfer tube (242), the main dimensions of which correspond for example to the main dimensions of the transfer tube (242) described in relation to the first exemplary embodiment, is integrated into the container adapter (200). The tip (243) of the tube, which protrudes in the direction of the container receptacle (221), is closed. The transfer tube (242) has a continuous transverse hole (245), the diameter of which corresponds, for example, to the diameter of the longitudinal hole (244) which is embodied, for example, as a tapering blind hole. The transverse hole (245) is aligned with two slide recesses (228) in the, for example cylindrical, side wall of the container receptacle (221). These slide recesses (228) are penetrated, for example during the manufacture of the container adapter (200), by two slides which hold the transfer tube (242) and generate the transverse hole (245). These slide recesses (228) are covered, for example by means of a valve hose (229).

A membrane cap (290), which is for example constructed like the cap (290) described in relation to the first exemplary embodiment, sits on the transfer tube (242) which is made, for example, of plastics material. The connecting tube hole (244) is thus closed in a sterile manner.

The container (250) is, for example, a glass bottle, or a lyophilisate bottle, with a waisted neck (259) and a flange edge (258). The flange edge (258) protrudes beyond the neck (259). However, the external diameter of the flange edge is smaller than the maximum external diameter of the container.

The transition between the neck (259) and the cylindrical outer wall of the container (250) is rounded with a large radius corresponding, for example, to twice the thickness of the container wall. The container (250) is secured to the container adapter (200) via a cap (230) and a tear-off banderole (260).

Figure 11:
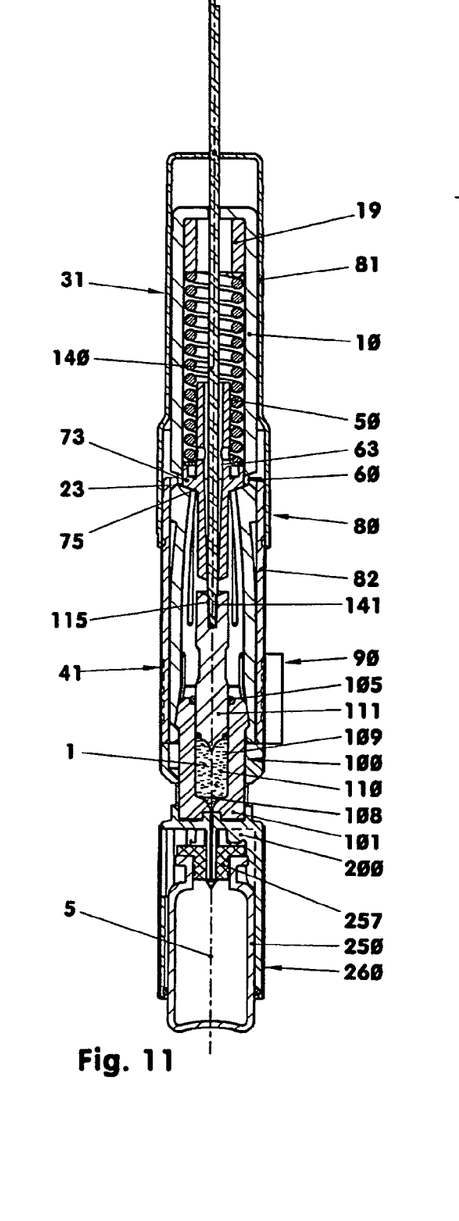
FIG. 11 shows the single-use injector and two-chamber system according to FIG. 8 after the transfer by pumping.

The opening (253) of the container (250) is closed, for example by a rubber container stopper (257). In the illustration of FIG. 11, the container stopper (257) has a stopper hole (254) which is closed by means of an external membrane (256). The diameter of the membrane (256) may, for example, be two millimeters larger than the aperture (254).

In order to be able to use the single-use injector, the active substance (2), for example the lyophilisate, stored in the container (250) must be dissolved in the liquid (1), for example water for injection purposes or physiological saline solution, present in the cylinder (101) of the cylinder/piston unit (100). For this purpose, the liquid (1) is to be pumped into the container (250).

In a first step, the tear-off lug (281) is removed from the cap (230), while severing the perforation (282), and the cap (230) is withdrawn from the rear part of the container (250).

Figures 8, 9, 10:
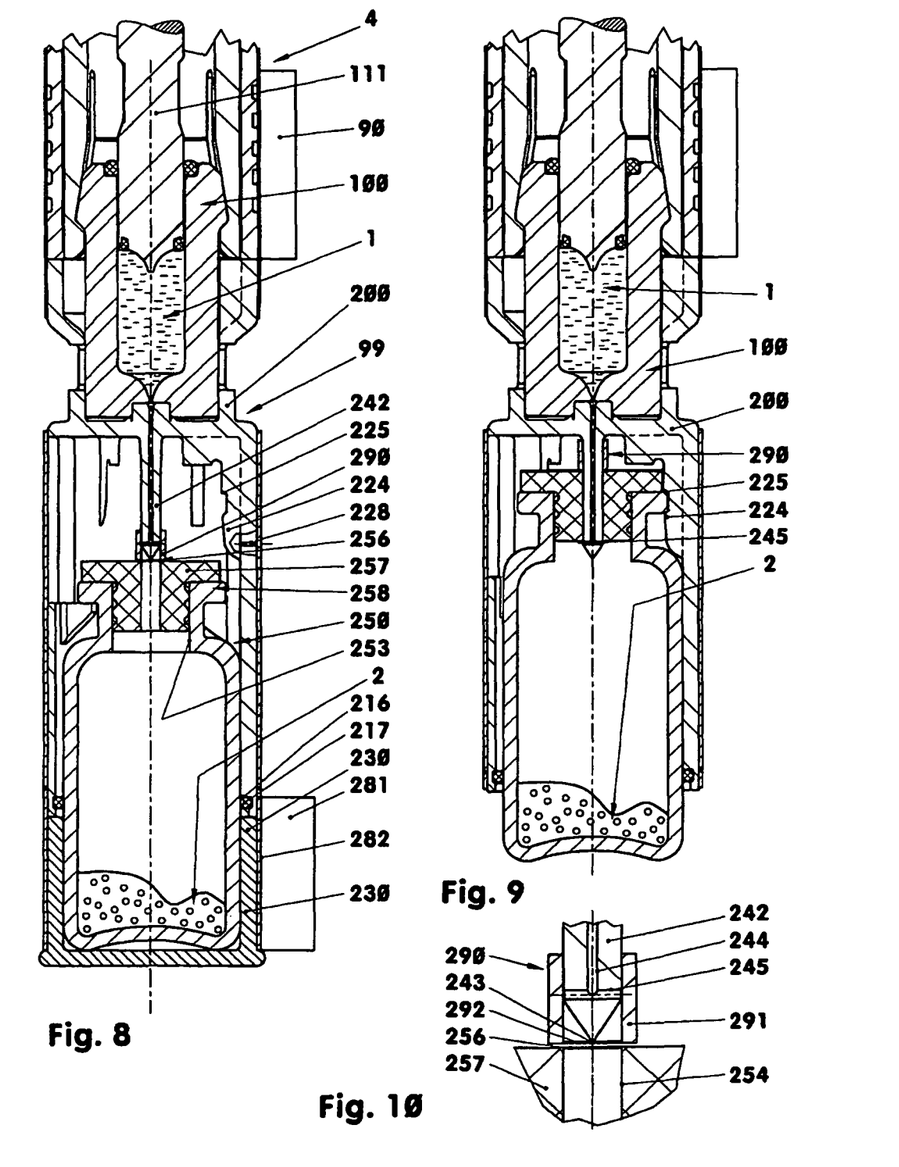
FIG. 8 shows the detail of a single-use injector and two-chamber system with a cylinder/piston unit.
FIG. 9 shows FIG. 8 after insertion of the container.
FIG. 10 shows the detail of the connecting tube and the stopper.

In the illustration of FIGS. 8 and 10, the container is arranged in such a way that the membrane (256) closes the aperture (254) of the stopper (257). The connecting tube (242) is closed by means of the membrane cap (290).

Figure 13:
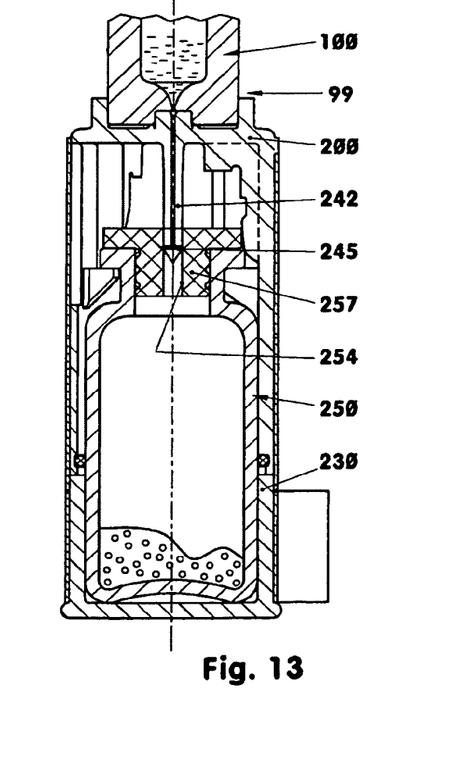
FIG. 13 shows the two-chamber system without a membrane.

If the individual components are, for example, manufactured simultaneously, the connecting tube (242) may protrude, after packing, into the stopper (257), cf. FIG. 13. The transverse hole (245) then lies in the aperture (254) and is closed by means of the stopper (257). This embodiment requires neither a membrane cap (290) nor a stopper membrane (256).

If appropriate, a resilient ring seal (217), which closes the joint between the container (250) and the inner wall of the container region (221) in a sterile manner, is located in an annular groove (216) of the container region (221).

Figure 12:
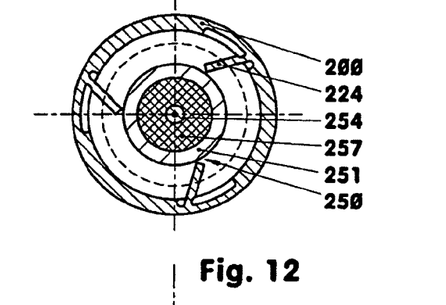
FIG. 12 is a cross section through the container adapter and the stopper.

In a second step, the container (250) is inserted into the container adapter (200). In this case, the container (250) slides forward on the inner wall of the container adapter (200) until its flange edge (258) rests against the stops (225), cf. FIG. 9. At the same time, the locking rear grips (224) surround the back of the flange edge (258) and thus secure the front position of the container (250). During the forward movement, the container (250) has pressed the folding locking hooks (223) to the side, cf. FIG. 6, and the locking hooks (224) interlock the container (250). FIG. 12 is a cross section of the container adapter (200) and of the inserted container (250). In this case, according to the exemplary embodiment of FIGS. 8 and 9, the transfer tube (242) penetrates both the cap membrane (292) and the container stopper membrane (256) and infiltrates the container (250). The cylinder interior (110) and the container interior (252) communicate via the transverse hole (245) and the hole (244) of the transfer tube (242). After perforation of the cap membrane (292), the membrane cap (290) is displaced along the transfer tube (242), upward in the illustration of FIG. 9. In an exemplary embodiment without membranes (256, 292), the connecting tube (242) penetrates the container interior (252), so that the transverse hole (245) protrudes from the stopper (257). The locking hooks (224) prevent extraction of the container (250).

The excess pressure produced when the container (250) is inserted in the container region (221) escapes via the slide recesses (228) with, for example, partial raising of the valve hose (229). The slide recesses (228) and the valve hose (229) thus have the function of an excess pressure valve.

In a third step, the piston (111) is pushed into the cylinder (101) by means of the pump rod (140) and the liquid (1) is thus conveyed into the container interior (252) which is now under slight excess pressure. For this purpose, the pump rod (140) is in general held carefully between the index finger and the thumb of the operating hand.

The lyophilisate (2) is dissolved in the liquid (1). The dissolving process can be visually monitored, as the container (250) protruding from the container adapter (200) is transparent.

In a fourth step, the newly produced solution (3) is pumped back into the cylinder interior (110). For this purpose, the injector is held in such a way that the opening (253) of the container (250) points in the direction of gravity. The piston (111) is drawn into a rear position via the pump rod (140). Bubble-free filling is checked via the windows (206), cf. FIG. 10.

In a fifth step, the tear-off banderole (94) is separated all the way round from the main part (92) and from the adapter part (93) with the aid of a tear-off lug (95), for releasing the single-use injector. The slots (57) of the triggering element (82) become visible. The container adapter (200) is now withdrawn from the cylinder (101), for example downward.

In a last step, the injector is placed onto the injection site and the sleeve-like triggering element (82) is pushed downward—in the direction of the injection site. The press rods (21) bend resiliently outward into their actual starting position. In this case, the cams (22) slip outward into the widening (83) via the edge (85). The press rods (21), which are now no longer deformed, release the piston actuating plunger (60), so that the piston (111) moves jerkily downward, under the action of the spring element (50), for draining the cylinder (101). As the piston (111) moves forward, the piston friction is reduced intermittently, as the rearward sealing element does not abut in a braking manner as it passes the waisted piston region.

Combinations of the exemplary embodiments described are also conceivable.

LIST OF REFERENCE NUMERALS

1 Water for injection purposes, solvent
2 Lyophilisate, active substance, pharmaceutical composition
3 Injection solution
4 Single-use injector
5 Centre line of the injector, longitudinal direction
6 Triggering movement direction of (82), downward movement direction arrow
7 Container insertion direction
10 Housing, one-piece
13 Outer surface, cylindrical, outer wall
19 Spacer sleeve
21 Press rods, support rods
22 Cams
23 Support surface
24 Abutment surface
28 Bending bar
31 Envelope region
33 Apertures
39 Floor
41 Fixing region for the cylinder/piston unit
42 Spring hook
43 Rear grip
50 Spring element, helical compression spring, spring energy store
57 Slots of (82)
59 Inner wall of (82)
60 Piston actuating plunger
62 Guide pin
63 Hole of plunger (60)
73 Plunger plate
75 Collar surface, conical
76 Piston slide
80 Triggering unit
81 Triggering cap
82 Triggering element, triggering sleeve
83 Widening
84 Set-back flank
85 Edge, sharp-edged
90 Tamper-proof closure, banderole, securing element, adhesive label
92 Edge part, rear; label part
93 Edge part, front; label part
94 Tear-off banderole
95 Tear-off lug
96 Perforations, predetermined breaking points
99 Two-chamber system
100 Cylinder/piston unit, first, injector-side
101 Cylinder, injector-side
102 Locking ring
103 End face
104 Adhesive ring
105 Chamber
106 Hole, nozzle
107 Recess in the end face
108 Cylinder floor
110 Cylinder interior
111 Piston 112 Annular groove
114 Ring seal, seal
115 Recess in (111)
119 Sterile filter membrane
132 Block button
140 Pump rod
141 Conical thread
200 Container adapter
201 Adapter region
204 Shoulder, annular
206 Window, on both sides
211 Intermediate floor
213 Elevation
216 Annular groove
217 Ring seal
221 Container region, container receptacle
223 Locking elements, folding locking hooks
224 Locking elements, locking rear grips
225 Stops
226 Windows
228 Slide recesses
229 Valve hose
230 Cap
242 Transfer tube, connecting tube
243 Tube tip
244 Hole, transfer tube hole
245 Transverse hole
250 Cylinder/piston unit, second, container
251 Tube, glass tube, plastics material tube
252 Cylinder interior, container interior
253 Opening
254 Stopper hole, aperture
255 Chamber
256 Membrane, stopper membrane
257 Stopper, resilient, rubber stopper
258 Flange edge
259 Notch, neck
261 Piston
262 Piston rod
263 Stopper carrier
264 Piston pressure plate
265 Locking elements
266 Collar
267 Piston stopper
268 Rubber ring, elastomer spring
280 Unwinding banderole
281 Tear-off lug
282 Perforation
290 Membrane cap
291 Wall region
292 Membrane, cap membrane

What is claimed is:

1. In combination with a single-use injector (4) and two-chamber system (99), including a housing (10), a cylinder/piston unit (100) operably retained by the housing (10) and comprising a cylinder (101) having a cylinder interior (110) initially filled with water (1) for injection purposes or subsequently filled with an injection solution (3) and having a first chamber (105), a piston (111) in operable arrangement in the rear of the cylinder (101), a spring-activated piston actuating plunger (60) operably arranged in the housing (10) in mechanical communication with the piston (111), the cylinder (101) including a floor having a nozzle-like hole (106) passing therethrough for needless injection, the piston actuating plunger (60) housed within the housing (10), a detachable container (250) having an inoperative or an operative position, the detachable container (250) when in the operative position in connective arrangement with but separated from and mounted outside of the housing (10) and when in the inoperative condition the detachable container (250) is detached from the housing (10), the detachable container (250) having a second chamber (255) having an interior (252) initially filled with an active substance (2), the detachable container (250) includes a stopper (257), the detachable container (250) closed at least temporarily by the stopper (257), a detachable container adapter (200) having an inoperative or an operative position, the detachable container adapter (200) when in the operative position detachably mounted between the housing (10) and the detachable container (250) and when in the inoperative position the detachable container adapter (200) is detached from both the housing (10) and the detachable container (250), the detachable container (250) in partial insertable relationship with the detachable container adapter (200) with the second chamber (255) positioned substantially outside of the detachable container adapter (200), the improvement which comprises:

the stopper (257) has a stopper hole (254) passing therethrough,
the detachable container adapter (200) includes an initially closed transfer tube (242),
the detachable container (250), upon insertion of the detachable container (250) in a container insertion direction (7) into operative engagement with the detachable container adapter (200), the transfer tube (242) passes through stopper hole (254) and connects in fluid communication the cylinder interior (110) of the cylinder/piston unit (100) to the interior (252) of the detachable container (250), and
means for causing the water (1) which initially filled the cylinder interior (110) to be removed from the cylinder interior (110) and transferred to the detachable container (250) upon the transfer tube (242) passing through the stopper hole (254) and for mixing the transferred water (1) with the active substance (2) for forming an injection solution (3) to be re-transferred to the cylinder interior (110) prior to use of the injector (4),
the transfer tube (242) is initially closed by means of a membrane cap (290) including a first non-liquid membrane (292),
the stopper hole (254) is initially closed by means of a second non-liquid membrane (256), and
the transfer tube (242) is initially closed by means of the membrane cap (290) including the first non-liquid membrane (292), the first non-liquid membrane (292) and the second non-liquid membrane (256) are in initial abutting contacting relationship with each other prior to insertion of the detachable container (250), when the detachable container (250) is inserted into the detachable container adapter (200), the transfer tube (242) pierces the first non-liquid membrane (256) and then the second non-liquid membrane (292).

2. In combination with a single-use injector (4) and two-chamber system (99), including a housing (10), a cylinder/piston unit (100) operably retained by the housing (10) and comprising a cylinder (101) having a cylinder interior (110) initially filled with water (1) for injection purposes or subsequently filled with an injection solution (3) and having a first chamber (105), a piston (111) in operable arrangement in the rear of the cylinder (101), a spring-activated piston actuating plunger (60) operably arranged in the housing (10) in mechanical communication with the piston (111), the cylinder (101) including a floor having a nozzle-like hole (106) passing therethrough for needless injection, the piston actuating plunger (60) housed within the housing (10), a detachable container (250) having an inoperative or an operative position, the detachable container (250) when in the operative position in connective arrangement with but separated from and mounted outside of the housing (10) and when in the inoperative condition the detachable container (250) is detached from the housing (10), the detachable container (250) having a second chamber (255) having an interior (252) initially filled with an active substance (2), the detachable container (250) includes a stopper (257), the detachable container (250) closed at least temporarily by the stopper (257), a detachable container adapter (200) having an inoperative or an operative position, the detachable container adapter (200) when in the operative position detachably mounted between the housing (10) and the detachable container (250) and when in the inoperative position the detachable container adapter (200) is detached from both the housing (10) and the detachable container (250), the detachable container (250) in partial insertable relationship with the detachable container adapter (200) with the second chamber (255) positioned substantially outside of the detachable container adapter (200), the improvement which comprises:

- the stopper (257) has a stopper hole (254) passing therethrough,
- the detachable container adapter (200) includes an initially closed transfer tube (242),
- the detachable container (250), upon insertion of the detachable container (250) in a container insertion direction (7) into operative engagement with the detachable container adapter (200), the transfer tube (242) passes through stopper hole (254) and connects in fluid communication the cylinder interior (110) of the cylinder/piston unit (100) to the interior (252) of the detachable container (250),
- means for causing the water (1) which initially filled the cylinder interior (110) to be removed from the cylinder interior (110) and transferred to the detachable container (250) upon the transfer tube (242) passing through the stopper hole (254) and for mixing the transferred water (1) with the active substance (2) for forming an injection solution (3) to be re-transferred to the cylinder interior (110) prior to use of the injector (4), and
- the transfer tube (242) comprises a closed tip (243), the transfer tube (242) has a longitudinal transfer tube hole (244) opening into a transverse hole (245) penetrating the transfer tube (242) proximate the closed tip (243), a membrane cap (290) having an elastically deformable wall region (291) and including a first membrane (292), the tip (243) is pointed and housed within the membrane cap prior to insertion into the detachable container (250) with the transverse hole (245) in sealed relationship with the wall region (291), a second membrane (256) is in initial closing relationship with the stopper hole (254), upon insertion the tip (243) pierces the first non-liquid membrane (292) and the second membrane (256) and passes through stopper hole (254).

3. The combination single-use injector (4) and two-chamber system (99) according to claim 2, wherein the detachable container adapter (200) further comprises a container receptacle (221) having at least two at least approximately radially oriented slide recesses (228), the transverse hole (245) is aligned with two of the slide recesses (228).

4. The combination single-use injector (4) and two-chamber system (99) according to claim 2, wherein the transfer tube (242) proximate the transverse tube hole (244) lies within the stopper hole (254) and the tip (243) seals the stopper hole (254) such that the transverse tube hole (244) is in fluid sealed relationship with the stopper (257) prior to the detachable container (250) being in operable engagement with the detachable container adapter (200) in the container insertion direction (7), whereby additional membranes for sealing the transfer tube (242) and stopper (257) are not required.

5. In combination with a single-use injector (4) and two-chamber system (99), including a housing (10), a cylinder/piston unit (100) operably retained by the housing (10) and comprising a cylinder (101) having a cylinder interior (110) initially filled with water (1) for injection purposes or subsequently filled with an injection solution (3) and having a first chamber (105), a piston (111) in operable arrangement in the rear of the cylinder (101), a spring-activated piston actuating plunger (60) operably arranged in the housing (10) in mechanical communication with the piston (111), the cylinder (101) including a floor having a nozzle-like hole (106) passing therethrough for needless injection, the piston actuating plunger (60) housed within the housing (10), a detachable container (250) having an inoperative or an operative position, the detachable container (250) when in the operative position in connective arrangement with but separated from and mounted outside of the housing (10) and when in the inoperative condition the detachable container (250) is detached from the housing (10), the detachable container (250) having a second chamber (255) having an interior (252) initially filled with an active substance (2), the detachable container (250) includes a stopper (257), the detachable container (250) closed at least temporarily by the stopper (257), a detachable container adapter (200) having an inoperative or an operative position, the detachable container adapter (200) when in the operative position detachably mounted between the housing (10) and the detachable container (250) and when in the inoperative position the detachable container adapter (200) is detached from both the housing (10) and the detachable container (250), the detachable container (250) in partial insertable relationship with the detachable container adapter (200) with the second chamber (255) positioned substantially outside of the detachable container adapter (200), the improvement which comprises:

- the stopper (257) has a stopper hole (254) passing therethrough,
- the detachable container adapter (200) includes an initially closed transfer tube (242),
- the detachable container (250), upon insertion of the detachable container (250) in a container insertion direction (7) into operative engagement with the detachable container adapter (200), the transfer tube (242) passes through stopper hole (254) and connects in fluid communication the cylinder interior (110) of the cylinder/piston unit (100) to the interior (252) of the detachable container (250),
- means for causing the water (1) which initially filled the cylinder interior (110) to be removed from the cylinder interior (110) and transferred to the detachable container (250) upon the transfer tube (242) passing through the stopper hole (254) and for mixing the transferred water (1) with the active substance (2) for forming an injection solution (3) to be re-transferred to the cylinder interior (110) prior to use of the injector (4), and
- the detachable container (250) is a second cylinder/piston unit (250).

* * * * *